(12) United States Patent
Li et al.

(10) Patent No.: US 11,779,917 B2
(45) Date of Patent: Oct. 10, 2023

(54) MICROFLUIDIC CHEMILUMINESCENCE IMMUNOASSAY ANALYZER

(71) Applicant: Shenzhen Watmind Medical Co., Ltd., Guangdong (CN)

(72) Inventors: Quan Li, Guangdong (CN); Runhua Jiang, Guangdong (CN); Fangbao Lu, Guangdong (CN); Xiaoyan Zhan, Guangdong (CN)

(73) Assignee: Shenzhen Watmind Medical Co., Ltd., Shenzhen (CN)

( * ) Notice: Subject to any disclaimer, the term of this patent is extended or adjusted under 35 U.S.C. 154(b) by 910 days.

(21) Appl. No.: 16/699,152

(22) Filed: Nov. 29, 2019

(65) Prior Publication Data

US 2020/0171493 A1     Jun. 4, 2020

(30) Foreign Application Priority Data

Nov. 29, 2018   (CN) .......................... 201811443519.1

(51) Int. Cl.
| | | |
|---|---|---|
| *B01L 3/00* | (2006.01) | |
| *G01N 21/76* | (2006.01) | |
| *G01N 27/74* | (2006.01) | |
| *G01N 21/15* | (2006.01) | |
| *G01N 33/543* | (2006.01) | |

(52) U.S. Cl.
CPC ... *B01L 3/502707* (2013.01); *B01L 3/502715* (2013.01); *G01N 21/15* (2013.01); *G01N 21/76* (2013.01); *G01N 27/745* (2013.01); *G01N 33/54366* (2013.01); *B01L 2200/025* (2013.01); *B01L 2200/027* (2013.01); *B01L 2200/028* (2013.01); *B01L 2300/0861* (2013.01); *B01L 2300/12* (2013.01); *B01L 2300/18* (2013.01)

(58) Field of Classification Search
CPC . B01L 3/502707; B01L 3/5027; G01N 21/76; G01N 27/745; G01N 33/54366
See application file for complete search history.

(56) References Cited

U.S. PATENT DOCUMENTS

| | | | |
|---|---|---|---|
| 11,215,610 B2* | 1/2022 | Gibbons | ............... B01L 3/5027 |
| 11,247,207 B2* | 2/2022 | Jokerst | ............ H01L 31/035281 |
| 2018/0003642 A1* | 1/2018 | Tomoda | ........... G01N 33/54326 |
| 2020/0096449 A1* | 3/2020 | Cheng | ..................... B01L 9/523 |

* cited by examiner

*Primary Examiner* — Brian J. Sines (57) ABSTRACT

The present disclosure provides a microfluidic chemiluminescence immunoassay analyzer which includes a detection box body provided with a dark room; a detection platform arranged within the dark room and configured to place a microfluidic chip, wherein a magnetic bead and a magnetic bead channel for placing the magnetic bead are arranged on the microfluidic chip; a magnet module arranged above the detection platform and capable of automatically adjusting the height of the magnet, wherein the magnet module is configured to collect and drag the magnetic bead within the magnetic bead channel; a pressing module arranged on the detection box body and configured to press a plurality of to-be-pressed portions of the microfluidic chip in a one-to-one correspondence manner by means of a plurality of motors; and a positioning module, arranged on the detection platform and configured to fix the microfluidic chip.

18 Claims, 6 Drawing Sheets

MICROFLUIDIC CHEMILUMINESCENCE IMMUNOASSAY ANALYZER

CROSS REFERENCE TO RELATED APPLICATIONS

The present application claims the benefit of Chinese Patent Application No. 201811443519.1 filed on Nov. 29, 2018, the contents of which are incorporated herein by reference in their entirety.

TECHNICAL FIELD

The present disclosure relates to the technical field of medical instruments, and particularly to a microfluidic chemiluminescence immunoassay analyzer.

BACKGROUND

Chemiluminescence immunoassay is the technique that detects and analyzes various antibodies, antigens, hormones, enzymes, and drugs by combining high sensitivity of the chemiluminescence technology with high specificity of an immunological method. The chemiluminescence immunoassay has the advantages of high speed, simplicity and convenience in operation, good repeatability, and no radioactive contamination because of using chemiluminescent substances as its markers. The chemiluminescence immunoassay technology has developed so far as an advanced and mature detection technology, occupying a huge market in the field of laboratory medicine.

At present, most of the chemiluminescence immunoassay analyzers used in the laboratory medicine is large-scale equipment. Although the test throughput is relatively high, the instrument is complicated in structure, large in volume and high in cost, and is not suitable for hospitals or testing institutions with small sample capacity. Therefore, it is necessary to develop a miniaturized chemiluminescence immunoassay analyzer.

SUMMARY

Embodiments of the present disclosure provide a microfluidic chemiluminescence immunoassay analyzer, which aims to solve the problem of large volume of a chemiluminescence immunoassay analyzer.

The objective is achieved as follows. The microfluidic chemiluminescence immunoassay analyzer includes:

a detection box body, which is provided with a dark room;

a detection platform, which is arranged within the dark room and configured to place a microfluidic chip, wherein a magnetic bead and a magnetic bead channel for placing the magnetic bead are arranged on the microfluidic chip;

a magnet module, which is arranged above the detection platform and is capable of adjusting the height of the magnet, wherein the magnet module is configured to collect and drag the magnetic bead within the magnetic bead channel;

a pressing module which is arranged on the detection box body and configured to press a plurality of to-be-pressed portions of the microfluidic chip in a one-to-one correspondence manner by means of a plurality of motors; and a positioning module, which is arranged on the detection platform and configured to fix the microfluidic chip.

Furthermore, the positioning module includes:

a first accommodating groove, which is provided on the top of the detection platform and configured to place the microfluidic chip;

an elastic positioning portion, which is arranged on the inner wall of the first accommodating groove and configured to abut against a corner of the microfluidic chip, wherein the elastic positioning portion pushes the microfluidic chip to enable the microfluidic chip to abut against two adjacent side walls of the first accommodating portion, and the two adjacent side walls, which abut against the microfluidic chip, of the first accommodating groove form a positioning surface; and a vertical limiting portion, which is arranged above the first accommodating groove and configured to fix the microfluidic chip.

Furthermore, the positioning module includes:

a second accommodating groove, which is provided on the side wall of the detection platform and configured to place the microfluidic chip, wherein the microfluidic chip is inserted within the second accommodating groove from the outside of the detection box body;

an elastic positioning pin, which is arranged on the bottom surface of the second accommodating groove and configured to fix the microfluidic chip, wherein the elastic positioning pin is provided with a guiding surface on an insertion side of the microfluidic chip;

an unlocking portion, which is arranged on the side wall of the detection platform and configured to unlock the elastic positioning pin; and an ejection portion, which is arranged within the dark room and configured to eject the microfluidic chip.

Furthermore, the magnet module includes:

a magnet, which is capable of sliding along the magnetic bead channel of the microfluidic chip after an end portion of the magnet abuts against the surface of the magnetic bead channel, so as to collect and drag the magnetic bead within the magnetic bead channel of the microfluidic chip;

a mounting block, which is configured to mount the magnet;

a first driving mechanism, which is configured to drive the mounting block and the magnet to move linearly;

a second driving mechanism, which is connected with the mounting block and configured to adjust the height of the mounting block; and a height adjusting mechanism, which is arranged between the mounting block and the magnet and configured to automatically finely adjust the height of the magnet.

Furthermore, one end of the mounting block is connected with the second driving mechanism and the other end thereof is provided with a stepped hole for allowing the magnet to slide up and down, and the stepped hole forms the height adjusting mechanism.

When the magnet slides along the magnetic bead channel, the height of the magnet is automatically finely adjusted while the magnet slides within the stepped hole.

Furthermore, the height adjusting mechanism includes:

a connecting block, which is configured to fixed connect with the magnet; and a rotating shaft which is configured to connect the connecting block and the mounting block.

The connecting block rotates about a shaft core of the rotating shaft after being pivotally connected with the mounting block.

When the magnet slides along the magnetic bead channel, the height of the magnet is automatically finely adjusted while the magnet rotates about the rotating shaft.

Furthermore, the pressing module includes:

a mounting platform, which is arranged above the detection platform;

a plurality of stepping motors, which are mounted on the mounting platform, wherein an adapter is connected to an output shaft of each stepping motor, a pressing block is connected to the other end of the adapter, and the pressing blocks are configured to press the plurality of to-be-pressed portions of the microfluidic chip in a one-to-one correspondence manner; and a controller, which is electrically connected with the plurality of stepping motors to control a pressing sequence of the output shafts of the stepping motors.

Furthermore, an access hole for allowing the detection platform in or out of the detection box body is provided on the side wall of the detection box body.

The access hole is sealed from the outside of the detection box body with a box door.

A linkage assembly is arranged between the detection platform and the box door. The linkage assembly enables the box door to be automatically opened or closed following the movement of the detection platform.

A driving motor for driving the detection platform in or out of the detection box body is further arranged within the dark room of the detection box body.

A light shielding portion is arranged between the detection box body and the box door. The light shielding portion surrounds the outside of the access hole.

Furthermore, the linkage assembly includes:

a sliding groove, which is provided on the detection platform and configured to extend along a moving direction of the detection platform;

a sliding shaft, which is configured to slide or rotate within the sliding groove; and a connecting rod, one end of which is fixedly connected with the sliding shaft and the other end of which is pivotally connected with the box door.

A sleeve, a first spring and a fixing ring are sequentially sleeved on the connecting rod.

The fixing ring is fixed at a distal end of the other end of the connecting rod.

An accommodating cavity for accommodating the first spring and the fixing ring is defined within the sleeve.

The sleeve is pivotally connected with the box door.

Furthermore, the light shielding portion includes a concave ring and a convex ring which are respectively arranged at the access hole of the detection box body and on the box door and are mutually matched.

The present disclosure at least has the following beneficial effects. In the embodiment of the present disclosure, the detection platform is arranged within the dark room, and the positioning module for fixing the microfluidic chip is arranged on the detection platform, so that the microfluidic chip is fixed within the dark room. The magnet module capable of automatically finely adjusting the height of the magnet is provided, and the height of the magnet is automatically adjusted according to the height of the magnetic bead channel of the microfluidic chip, so that the magnetic bead is precisely controlled. Moreover, the plurality of to-be-pressed portions of the microfluidic chip are pressed by means of the plurality of motors in a one-to-one correspondence manner, such that a pressing sequence may be arbitrarily adjusted as needed. Accordingly, the microfluidic chemiluminescence immunoassay analyzer is suitable for various microfluidic chips for different detection purposes. Compared with a large-scale fully automatic chemiluminescence instrument, the microfluidic chemiluminescence immunoassay analyzer provided by the embodiment of the present disclosure is greatly simplified in structure, small in volume, low in manufacturing cost, and convenient to operate. Compared with a semi-automatic chemiluminescence instrument, the microfluidic chemiluminescence immunoassay analyzer greatly reduces the artificial operation, so as to be relatively high in testing speed and relatively accurate in results. The microfluidic chemiluminescence immunoassay analyzer may realize real-time on-site detection around patients and quickly obtain diagnostic results. Therefore, the microfluidic chemiluminescence immunoassay analyzer is very suitable for use in ICUs of hospitals, emergency departments, clinics, small and medium-sized hospitals, social welfare centers, and homes of the patients.

DESCRIPTION OF THE EMBODIMENTS

In order to make the objective, technical solution and advantages of the present disclosure relatively clear and apparent, the present disclosure will be further described in detail below with reference to accompanying drawings and embodiments. It should be understood that the specific embodiments described herein are merely illustrative of the present disclosure and are not intended to limit the present disclosure.

A microfluidic chemiluminescence immunoassay analyzer implemented by the present disclosure is a general analysis platform, and may be used for detecting various kinds of immunization items such as cardiac markers, tumor markers, thyroid functions and reproductive endocrine hormones by replacing different microfluidic chips.

In the embodiment of the present disclosure, a detection platform is arranged within a dark room, and a positioning module for fixing a microfluidic chip is arranged on the detection platform, so that the microfluidic chip is fixed within the dark room. A magnet module capable of automatically finely adjusting the height of a magnet is arranged above the detection platform and configured to collect and drag a magnetic bead within a magnetic bead channel of the microfluidic chip, so that the magnetic bead is precisely controlled. Moreover, a plurality of to-be-pressed portions of the microfluidic chip are pressed in a one-to-one correspondence manner by means of a plurality of motors arranged on the detection box body, such that a pressing sequence may be arbitrarily adjusted as needed. Accordingly, the microfluidic chemiluminescence immunoassay analyzer is suitable for various microfluidic chips for different detection purposes. Compared with a large-scale fully automatic chemiluminescence instrument, the microfluidic chemiluminescence immunoassay analyzer provided by the embodiment of the present disclosure is greatly simplified in structure, small in volume, low in manufacturing cost, and convenient to operate. Compared with a semi-automatic chemiluminescence instrument, the microfluidic chemiluminescence immunoassay analyzer greatly reduces the artificial operation, so as to be relatively high in testing speed and relatively accurate in results. The microfluidic chemiluminescence immunoassay analyzer is very suitable for use in ICUs of hospitals, emergency departments, clinics, small and medium-sized hospitals, social welfare centers, and homes of patients.

First Embodiment

Figure 1:
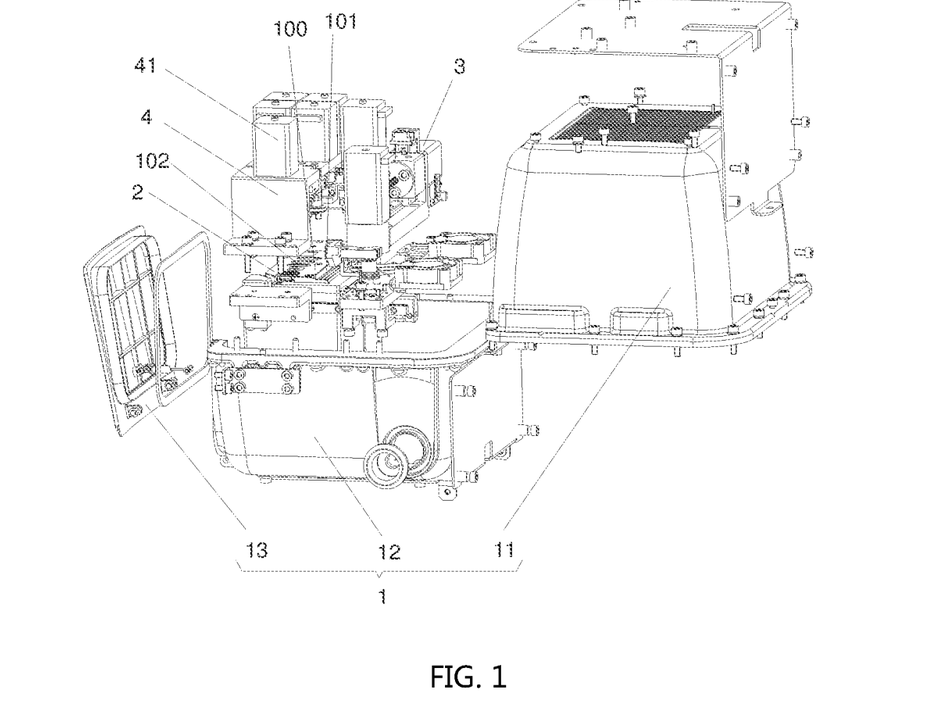
FIG. 1 is a schematic exploded diagram showing a structure of a microfluidic chemiluminescence immunoassay analyzer according to a first embodiment of the present disclosure.

As shown in FIG. 1, an embodiment of the present disclosure provides a microfluidic chemiluminescence immunoassay analyzer, including a detection box body 1, which is provided with a dark room; a detection platform 2, which is arranged within the dark room and configured to place a microfluidic chip, wherein a magnetic bead and a magnetic bead channel 101 for placing the magnetic bead are arranged on the microfluidic chip 100; a magnet module 3, which is arranged above the detection platform 2 and is capable of automatically finely adjusting the height of the magnet, wherein the magnet module 3 is configured to collect and drag the magnetic bead within the magnetic bead channel of the microfluidic chip; a pressing module 4, which is arranged on the detection box body 1 and configured to press a plurality of to-be-pressed portions of the microfluidic chip in a one-to-one correspondence manner by means of a plurality of motors 41; and a positioning module, which is arranged on the detection platform 2 and configured to fix the microfluidic chip 100. The magnetic bead, the magnetic bead channel 101 for placing the magnetic bead, and the plurality of to-be-pressed portions 102 are arranged on the microfluidic chip 100. Various testing agents are loaded within the to-be-pressed portions 102.

The detection box body includes an upper box body 11, a lower box body 12 and a box door 13. Concave cavities are respectively arranged on the upper box body 11 and the lower box body 12. The upper box body 11, the lower box body 12 and the box door 13 are fastened. A joint among the upper box body 11, the lower box body 12 and the box door 13 is subjected to a light shielding treatment to form the dark room. There are many light shielding treatments, for example, a sealant is placed at the joint among the upper box body 11, the lower box body 12 and the box door 13, or a concave ring and a convex ring which are mutually matched are arranged on the joint among the upper box body 11, the lower box body 12 and the box door 13, and the like.

The analyzer further includes a temperature control module, an optical signal detection module and a control circuit module. The temperature control module consists of a heating plate, a temperature sensor, an overheat protection switch and a fan, and provides a suitable temperature for a chemical reaction within the microfluidic chip. The optical signal detection module includes a chemiluminescence signal detector and a light shutter, wherein the chemiluminescence signal detector is a photomultiplier tube, which is positioned under the microfluidic chip, and a photosensitive surface of the photomultiplier tube is closely attached to a light emitting window at the bottom of the microfluidic chip; a plurality of switching hole positions, including an obstruction position, an all-pass position and a filter position, are arranged on the light shutter and are controlled to be switched by the stepping motors. The pressing module, the magnet module, the temperature control module and the optical signal detection module are all connected with a circuit control analysis module to realize automatic control of corresponding functions and analysis processing of signals. Since the temperature control module, the optical signal detection module and the control circuit module are conventional modules of the microfluidic chemiluminescence immunoassay analyzer, specific structures, connection relationships, and circuits of the above modules will be omitted here.

In the embodiment of the present disclosure, the detection platform 2 is arranged within the dark room, and the positioning module for fixing the microfluidic chip 100 is arranged on the detection platform 2, so that the microfluidic chip 100 is fixed within the dark room. The magnet module 3 capable of automatically finely adjusting the height of the magnet is provided, and the height of the magnet is automatically adjusted according to the height of the magnetic bead channel of the microfluidic chip, so that the magnetic bead is precisely controlled. Moreover, the plurality of to-be-pressed portions of the microfluidic chip are pressed in a one-to-one correspondence manner by means of the plurality of motors 41, so that a pressing sequence may be arbitrarily adjusted as needed. Accordingly, the microfluidic chemiluminescence immunoassay analyzer is suitable for various microfluidic chips for different detection purposes. Compared with a large-scale fully automatic chemiluminescence instrument, the microfluidic chemiluminescence immunoassay analyzer provided by the embodiment of the present disclosure is greatly simplified in structure, small in volume, low in manufacturing cost, and convenient to operate. Compared with a semi-automatic chemiluminescence instrument, the microfluidic chemiluminescence immunoassay analyzer greatly reduces the artificial operation, so as to be relatively high in testing speed and relatively accurate in results. The microfluidic chemiluminescence immunoassay analyzer may realize real-time on-site detection around the patients and quickly obtain diagnostic results. Therefore, the microfluidic chemiluminescence immunoassay analyzer is very suitable for use in ICUs of hospitals, emergency departments, clinics, small and medium-sized hospitals, social welfare centers, and homes of the patients.

Second Embodiment

Figure 2:
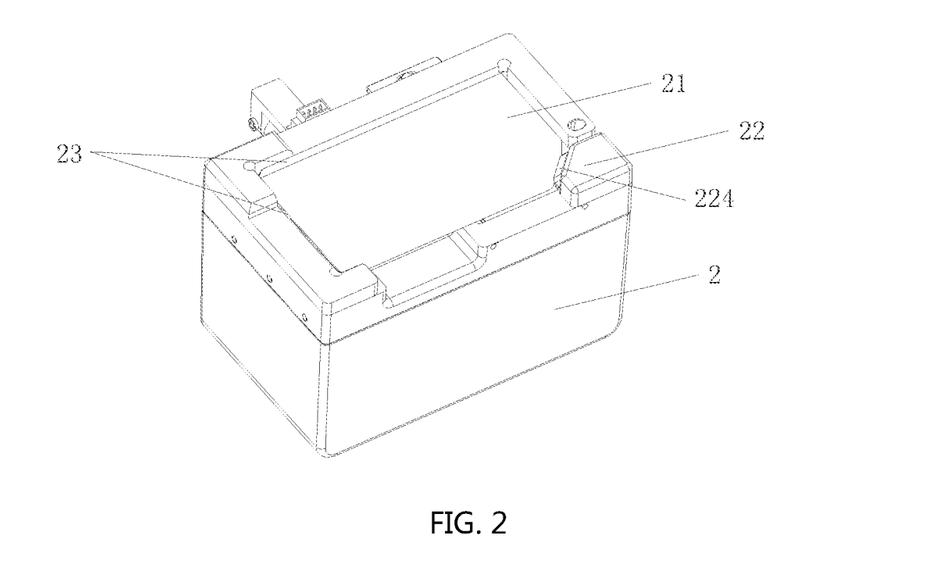
FIG. 2 is a schematic diagram showing a structure of a detection platform according to a second embodiment of the present disclosure.

As shown in FIG. 2, on the basis of the first embodiment, the positioning module includes a first accommodating groove 21, which is provided on the top of the detection platform 2 and configured to place the microfluidic chip 100; an electric positioning portion 22, which is arranged on the inner wall of the accommodating groove 21 and configured to abut against a corner of the microfluidic chip 100, wherein the elastic positioning portion 22 pushes the microfluidic chip 100 to enable the microfluidic chip 100 to abut against two adjacent side walls of the first accommodating groove 21, and the two adjacent sidewalls, which abut against the microfluidic chip 100, of the first accommodating groove 21 form a positioning surface; and a vertical limiting portion (not shown), which is arranged above the first accommodating groove 21 and configured to fix the microfluidic chip 100. In this embodiment, the first accommodating groove 21 is a cavity opened at the top of the detection platform 2, and the microfluidic chip 100 is placed within the first accommodating groove 21 from top to bottom.

Figure 3:
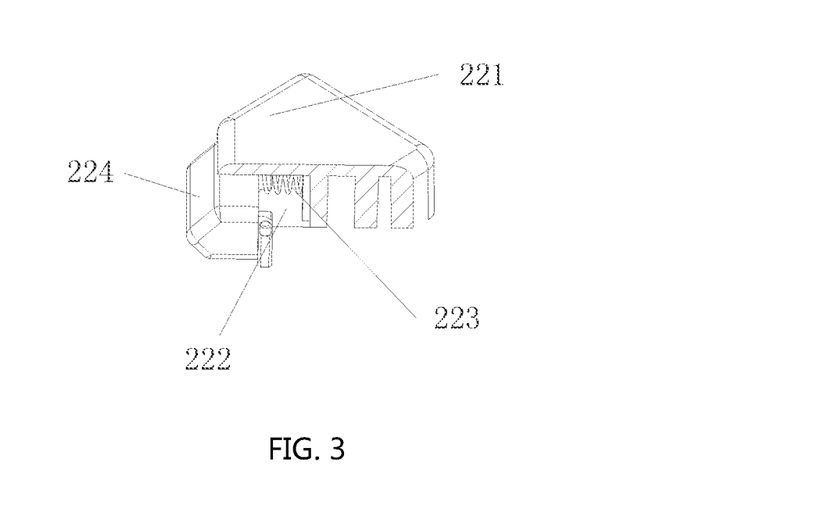
FIG. 3 is a schematic partial cross-sectional view showing a structure of a detection platform according to the second embodiment of the present disclosure.

As shown in FIG. 3, the elastic positioning portion 22 includes a fixing block 221 provided with a hollow cavity 222, a second spring 223 placed within the hollow cavity 222 and having one end abutting against the inner wall of the hollow cavity 222, and a movable block 224 abutting against the other end of the second spring 223. The movable block is further provided with a chamfer 225 at one side of the first accommodating groove 21. When the microfluidic chip is placed into the first accommodating groove 21 from the upside of the first accommodating groove 21, a force may be applied to the chamfer 225 by the microfluidic chip, so that the movable block 224 and the second spring 223 are pressed to retract the movable block 224 into the hollow cavity 222. The microfluidic chip enters the first accommodating groove 21, and at this moment, the second spring 223 pushes the movable block 224 and further pushes the microfluidic chip, so that the microfluidic chip abuts against the two adjacent side walls of the first accommodating groove 21 as the positioning surface 23.

The vertical limiting portion includes a linear motor arranged above the first accommodating groove 21. After the microfluidic chip is placed within the first accommodating groove 21, an output shaft of the linear motor presses against the microfluidic chip and the microfluidic chip is fixed in a vertical direction.

Third Embodiment

Figure 4:
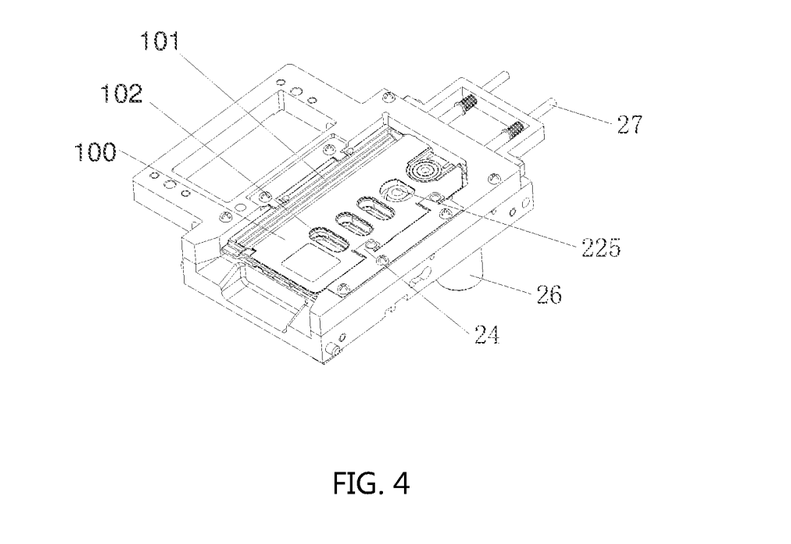
FIG. 4 is a schematic diagram showing a structure of a detection platform according to a third embodiment of the present disclosure.
Figure 5:
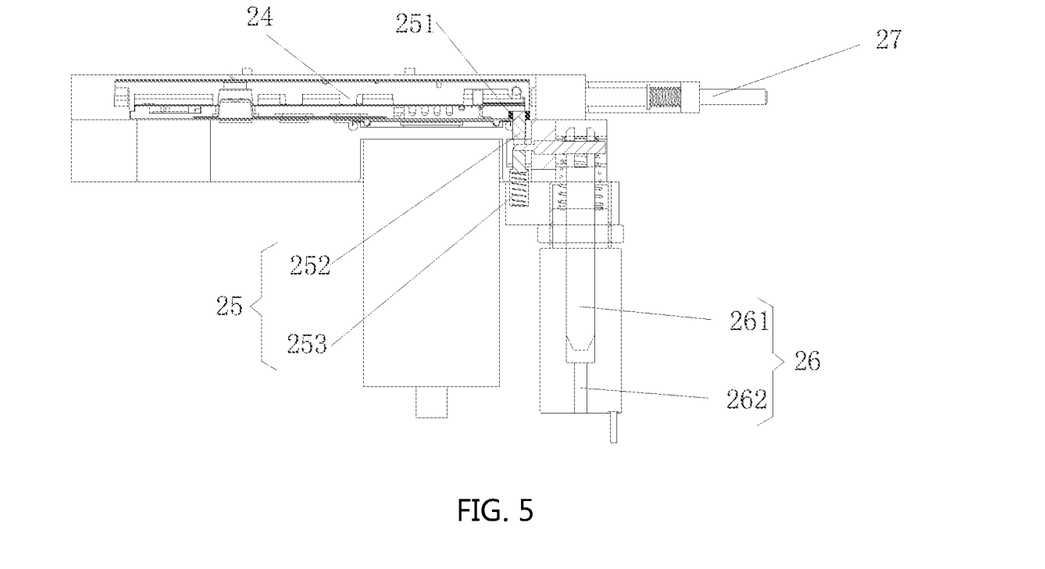
FIG. 5 is a schematic cross-sectional view showing a structure of a detection platform according to a third embodiment of the present disclosure.

As shown in FIG. 4 and FIG. 5, on the basis of the first embodiment, the positioning module includes a second accommodating groove 24, which is provided on the side wall of the detection platform 2 and configured to place the microfluidic chip 100, wherein the microfluidic chip 100 is inserted within the second accommodating groove 24 from the outside of the detection box body; an electric positioning pin 25, which is arranged at the bottom surface of the second accommodating groove 24 and configured to fix the microfluidic chip 100, wherein the elastic positioning pin 25 is provided with a guiding surface 251 on an insertion side of the microfluidic chip 100; an unlocking portion 26, which is positioned on the side wall of the detection platform 2 and configured to unlock the elastic positioning pin 25; and an ejection portion 27, which is arranged within the dark room and configured to eject the microfluidic chip 100. In this embodiment, the second accommodating groove 24 is a cavity opened on the side surface of the detection platform 2, and the microfluidic chip is inserted within the second accommodating groove 24 of the detection platform 2 from the outside of the detection box body.

Particularly, the elastic positioning pin 25 includes a movable pin 252, which is partially exposed within the second accommodating groove 24; and a third spring 253, which is arranged at the lower portion of the pin 252. The guiding surface 251 is arranged on the pin 252. A positioning hole for the insertion of the pin 252 is provided on the microfluidic chip. The unlocking portion 26 is a mechanism for providing the pin 252 with an elastic force against the third spring 253, which may use a motor or an electromagnet 261 or the like. For example, the electromagnet 261 is connected with the pin 252 by using the electromagnet 261. When there is need for unlocking, the electromagnet 261 is energized, then generates a magnetic force, and attracts a magnetic substance 262 below each other, so as to drive the pin 252 to move downwards against the elastic force of the third spring 253, so that the unlocking purpose is achieved. There are many structures of the unlocking portion 26, which will be omitted here.

The ejection portion 27 includes an ejection rod and a motor (not shown).

The microfluidic chip presses against the guiding surface 251 during insertion, and further compresses the third spring 253, to enable the pin 252 to move downwards. After the microfluidic chip is inserted into a predetermined position, the pin 252 upwards moves under an action of an elastic restoring force of the third spring 253. The microfluidic chip is fixed after being inserted within a positioning hole of the microfluidic chip. When there is a need for taking the microfluidic chip out, the unlocking portion 26 drives the pin 252 to move downwards against the elastic force of the third spring 253, so that the pin 252 is disengaged from the positioning hole of the microfluidic chip, and then the microfluidic chip is ejected out by means of the ejection portion 27.

Fourth Embodiment

Figure 6:
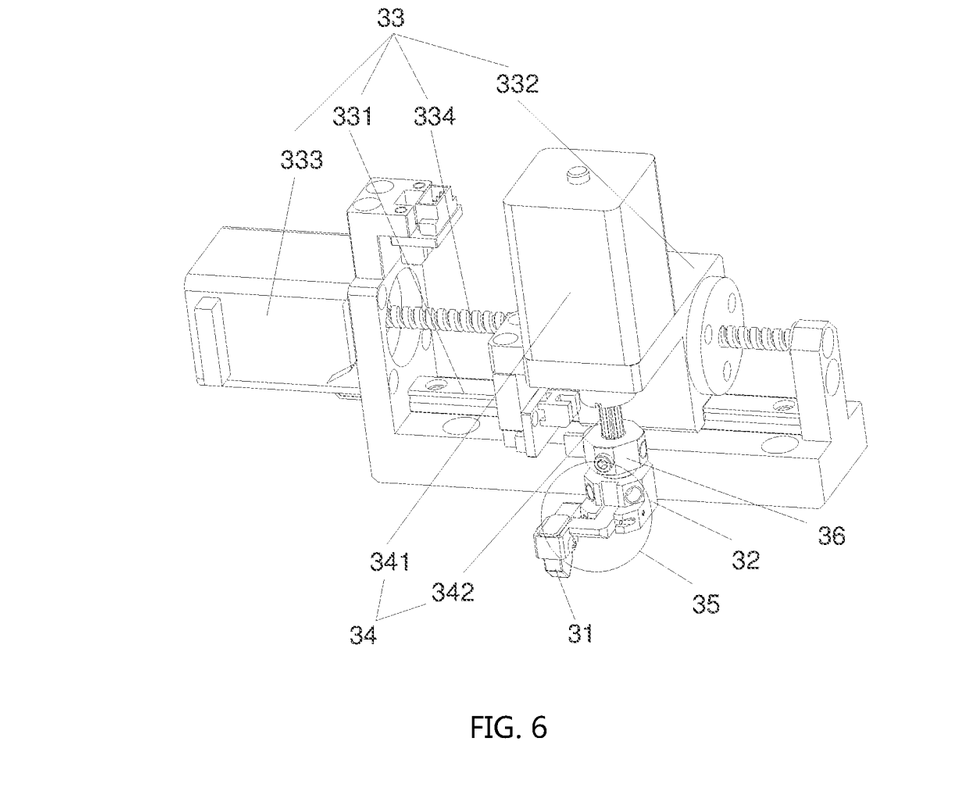
FIG. 6 is a schematic diagram showing a structure of a magnet module according to a fourth embodiment of the present disclosure.

As shown in FIG. 6, on the basis of the first embodiment, the magnet module 3 includes a magnet 31, which is capable of sliding along the magnetic bead channel of the microfluidic chip after an portion of the magnet 31 abuts against the surface of the magnetic bead channel and is configured to collect and drag the magnetic bead within the magnetic bead channel of the microfluidic chip; a mounting block 32, which is configured to mount the magnet 31; a first driving mechanism 33, which is configured to drive the mounting block 32 and the magnet 31 to move linearly; a second driving mechanism 34, which is connected with the mounting block 32 and configured to adjust the height of the mounting block 32; and a height adjusting mechanism 35, which is arranged between the mounting block 32 and the magnet 31 and configured to automatically finely adjust the height of the magnet 31.

In this embodiment, the magnetic bead and the magnetic bead channel for placing the magnetic bead are arranged on the microfluidic chip. When the magnet module 3 is in operation, the second driving mechanism drives the mounting block 32 to move in a vertical direction, so that the magnet on the mounting block 32 is placed on the magnetic bead channel. When the magnet module 3 moves, the magnet 31 in the magnet module 3 may collect and drag the magnetic bead, so that a sample is conveniently detected. Particularly, in this embodiment, the mounting block 32 is connected with the second driving mechanism 34. Therefore, the first driving mechanism 33 drives the second driving mechanism 34 to move linearly while driving the mounting block 32 to move linearly. When the first driving mechanism 33 drives the mounting block 32 to move linearly, the magnet 31 on the mounting block 32 may be driven to move linearly on the magnetic bead channel, so as to collect and drag the magnetic bead. When the second driving mechanism 34 drives the mounting block 32 to move in the vertical direction, the magnet 31 on the mounting block 32 is moved away from the magnetic bead channel, so that the magnetic bead is released.

Further, in this embodiment, the height adjusting mechanism 35 is arranged between the mounting block 32 and the magnet 31, and the height adjusting mechanism 35 may automatically finely adjust the height of the magnet 31. When the magnet moves on the magnetic bead channel, even if surface heights of the magnetic bead channel are inconsistent, the height of the magnet 31 may be automatically adjusted, so that the magnet 31 is closely attached to the surface of the magnetic bead channel. Accordingly, the stability of a detection process is ensured and the detection accuracy is improved.

Alternatively, in this embodiment, a fixing platform 32 is further arranged above the mounting block 32 for fixing the mounting block 32 to prevent the mounting block 32 from being played up and down along an output shaft 342 of the second driving mechanism 34. The fixing platform may employ a nut or may employ other fasteners capable of fixing the mounting block 32.

Certainly, in this embodiment, a sensor may be arranged on the first driving mechanism 33 and the second driving mechanism 34 to sense whether the first driving mechanism 33 and the second driving mechanism 34 are installed in place.

In this embodiment, the first driving mechanism 33 includes a linear sliding rail 331; a sliding block 332 fixedly connected with the mounting block 32; and a linear driving motor 333 driving the sliding block 332 to reciprocate along the linear sliding rail 331. In a specific implementation, the linear driving motor 333 drives the sliding block 332 to linearly move on the linear sliding rail 331. The sliding block 332 drives the mounting block 32 to linearly move during movement, and the mounting block 32 drives the magnet 31 to linearly move on the magnetic bead channel for detecting a sample.

Alternatively, in this embodiment, the second driving mechanism 34 may be arranged between the sliding block 332 and the mounting block 32. Further, when the sliding block 332 linearly moves, it may drive the second driving mechanism 34 to linearly move along with the mounting block 32. The second driving mechanism 34 drives the mounting block 32 to move in the vertical direction. There is no interference between movements in both directions. Accordingly, the second driving mechanism is compact in structure.

In this embodiment, an output screw 334 is arranged on the linear driving motor 333, and an internal thread screwed with the output screw is arranged on the sliding block 332. Particularly, when the linear driving motor 333 controls the output screw 334 to rotate forwards or reversely, the sliding block 332 screwed with the output screw 334 may reciprocate on the linear sliding rail 331 and further drive the mounting block 32 to linearly reciprocate. In this embodiment, the movement of the sliding block 332 is controlled in a screwing form, so that the sliding block 332 may move more stably, and further the stability of the movement of the magnet 31 on the magnetic bead channel is ensured.

In this embodiment, the second driving mechanism 34 includes a linear motor 341, wherein the mounting block 32 is fixedly connected with the output shaft 342 of the linear motor 341. In this embodiment, the linear motor 341 controls the output shaft 342 to move in the vertical direction, and the output shaft 342 may drive the mounting block 32 to move in the vertical direction. When the linear motor 341 controls the output shaft 342 to move upwards, the magnet 31 is moved away from the magnetic bead channel and further the magnetic bead is released. When the linear motor 341 controls the output shaft 342 to move downwards, the magnet 31 is placed on the magnetic bead channel. When the magnet module 3 moves, the magnet 31 may collect and drag the magnetic bead for conveniently detecting a sample.

Alternatively, in this embodiment, the output shaft 342 of the linear motor 341 may employ the screw. Correspondingly, an internal thread may be arranged on the mounting block 32 as well. This embodiment does not limit a specific form of the output shaft 342.

Fifth Embodiment

As shown in FIG. 6, on the basis of the fourth embodiment, in this embodiment, one end of the mounting block 32 is connected with the second driving mechanism 34, and the other end thereof is provided with the stepped hole. The stepped hole constitutes the height adjusting mechanism 35. The stepped hole is arranged in the vertical direction. A step matching with the stepped hole is arranged outside the magnet 31, that is, the magnet 31 may move up and down in the stepped hole according to the surface heights of the magnetic bead channel, so that the height of the magnet 31 is adjusted. Accordingly, the height adjusting mechanism is simple in structure. When the second driving mechanism 34 drives the mounting block 32 to move in the vertical direction, the step of the stepped hole supports the magnet 31 together away from the magnetic bead channel.

Sixth Embodiment

Figure 7:
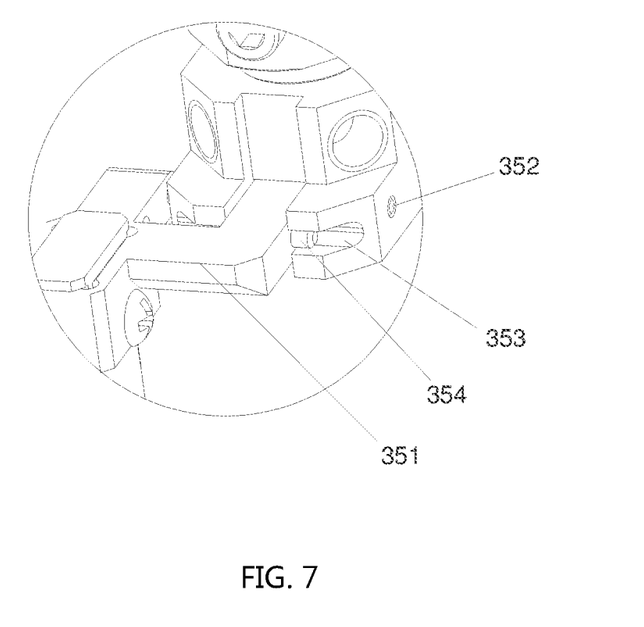
FIG. 7 is a schematic diagram showing a structure of a height adjusting mechanism according to a sixth embodiment of the present disclosure.

As shown in FIG. 6 and FIG. 7, on the basis of the fourth embodiment, in this embodiment, the height adjusting mechanism 35 includes a connecting block 351, which is configured to fixedly connect the magnet 31; and a rotating shaft 352, which is configured to connect the connecting block 351 and the mounting block 32, wherein the connecting block rotates about a shaft core of the rotating shaft 352 after being pivotally connected with the mounting block 32. In this embodiment, the magnet 31 is connected with the mounting block 32 through the connecting block 351, and the rotating shaft 352 is arranged in the mounting block 32. The rotating shaft 352 is laterally overlapped in a through hole of the mounting block 32, or may be fixed on the mounting block 32, or may be movably arranged on the mounting block 32. Since the connecting block 351 is pivotally connected with the rotating shaft 352, the connecting block 351 may rotate about the shaft core of the rotating shaft 352. When the surface heights of the magnetic bead channel are relatively small, the magnet 31 may move downwards due to its own weight, and the connecting block 351 rotates downwards about the shaft core of the rotating shaft 352, so that the magnet 31 is closely attached to the surface of the magnetic bead channel. When the surface heights of the magnetic bead channel are relatively large, the magnetic bead channel will push the magnet 31 upwards, so that the magnet 31 is closely attached to the surface of the magnetic bead channel, the connecting block 351 will rotate upwards about the shaft core of the rotating shaft 352, and thus the purpose of automatically finely adjusting the height of the magnet 31 is achieved. The entire height adjusting mechanism 35 in this embodiment is simple in structure and is easy to implement.

Alternatively, this embodiment does not limit a specific manner in which the connecting block 351 is pivotally connected with the rotating shaft 352, and may employ the most common manner in which the connecting block 351 is pivotally connected with the rotating shaft 352 via a shaft hole. Certainly, other manners should fall within the scope of protection of the present disclosure as well. Similarly, in this embodiment, the magnet 31 may be fixed with the connecting block 351 by employing a bolt or other means.

In this embodiment, the height adjusting mechanism 35 further includes an angular limiting portion, which is configured to limit a range of a rotation angle of the connecting block 351. Since the height adjusting mechanism 35 in this embodiment finely adjusts the height of the magnet 31, the angular limiting portion is provided to limit the rotation of the connecting block 351, so as to prevent the magnet 31 from being completely disengaged from the magnetic bead channel due to a large rotational amplitude of the connecting block 351 when the magnet 31 linearly moves on the magnetic bead channel, facilitating to ensure the stability of the movement of the magnet 31.

In this embodiment, particularly, the angular limiting portion includes a limiting groove 353, which is provided on the mounting block 32; and a limiting rod 354, which is arranged on the connecting block 351, wherein when the connecting block 351 rotates about the shaft core of the rotating shaft 352, the limiting rod 354 moves within the limiting groove 353.

Alternatively, in this embodiment, the limiting rods 354 are arranged on both sides of the connecting block 351. Correspondingly, two limiting grooves 353 are further provided on the mounting block 32 as well to enable the connecting block 351 to rotate about the rotating shaft 352 relatively stably.

Seventh Embodiment

Figure 8:
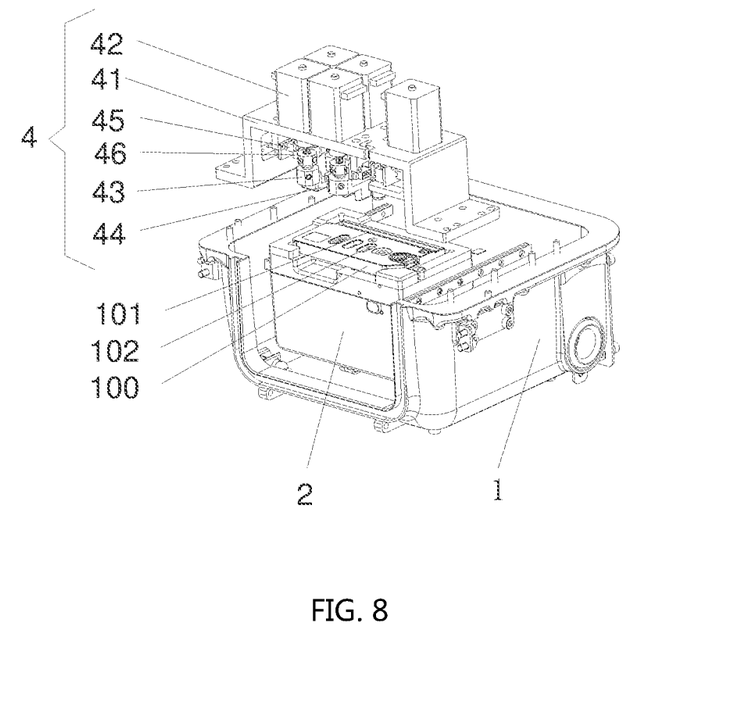
FIG. 8 is a schematic diagram showing a structure of a microfluidic chemiluminescence immunoassay analyzer according to a seventh embodiment of the present disclosure.

As shown in FIG. 8, on the basis of the first embodiment, the pressing module 4 includes a mounting platform 41, which is arranged above the detection platform 2; a plurality of stepping motors 42, which are mounted on the mounting platform 41, wherein an adapter 43 is connected to an output shaft of each stepping motor 42, a pressing block 44 is connected to the other end of the adapter, and the pressing block is configured to press a plurality of to-be-pressed portions of the microfluidic chip in a one-to-one correspondence manner; and a controller, which are electrically connected with the plurality of stepping motors 42 to control a pressing sequence of the output shaft of each stepping motor 42.

In this embodiment, the mounting platform 41 functions to carry the entire pressing module 4, and the adapter 43 is configured to integrate the output shafts of the plurality of stepping motors 42, so that the size of an arrangement space of the plurality of output shafts is reduced. The pressing blocks 44 of the stepping motors 42 may be arranged correspondingly to the to-be-pressed portions at different positions on the microfluidic chip respectively, so that when the microfluidic chip is pressed, the pressing module 4 can press the to-be-pressed portions at different positions on the microfluidic chip. Particularly, when there is a need for pressing the to-be-pressed portions of the microfluidic chip, the controller controls the adapters 43 on the different stepping motors 42 to drive the pressing blocks 44 to press the to-be-pressed portions at different positions on the microfluidic chip correspondingly, so that the pressing sequence of the to-be-pressed portions of the microfluidic chip is flexibly adjusted.

Alternatively, the pressing module 4 further includes a sensor 45, which is electrically connected with the controller, wherein a triggering block 46 corresponding to the sensor 45 is arranged on the output shaft of the stepping motor 42. The sensor 45 transmits a sensing signal to the controller when sensing the triggering block 46, so as to control the stepping motor 42 to make an action. In this embodiment, when the sensor 45 senses the triggering block 46, the sensor 45 senses an initial position of the output shaft of the stepping motor 42 through the triggering block 46, and transmits the signal to the controller. The controller controls different stepping motors 42 to drive the pressing blocks 44 thereon to press the to-be-pressed portions of the microfluidic chip. The sensor 45 is a photoelectric sensor.

Eighth Embodiment

Figure 9:
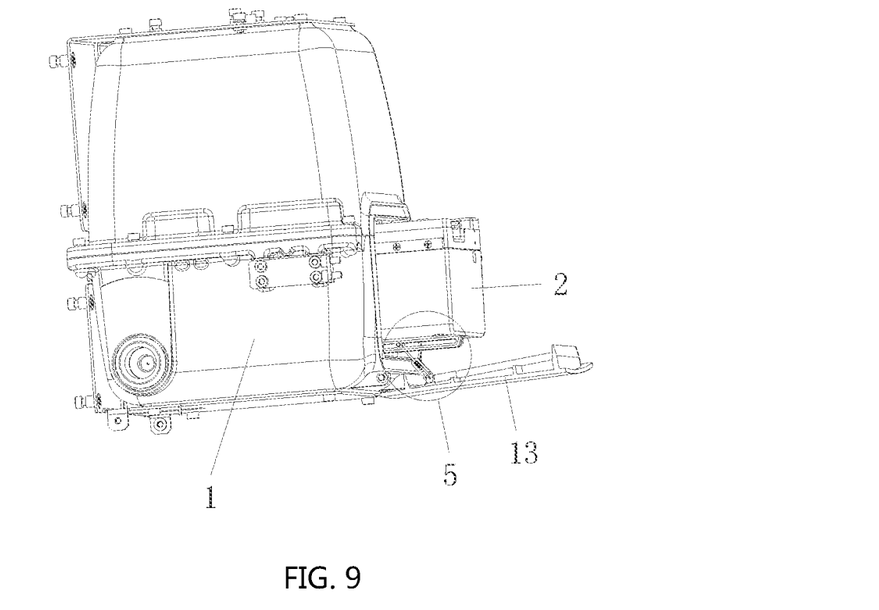
FIG. 9 is a schematic diagram showing a structure of a microfluidic chemiluminescence immunoassay analyzer according to an eighth embodiment of the present disclosure.
Figure 10:
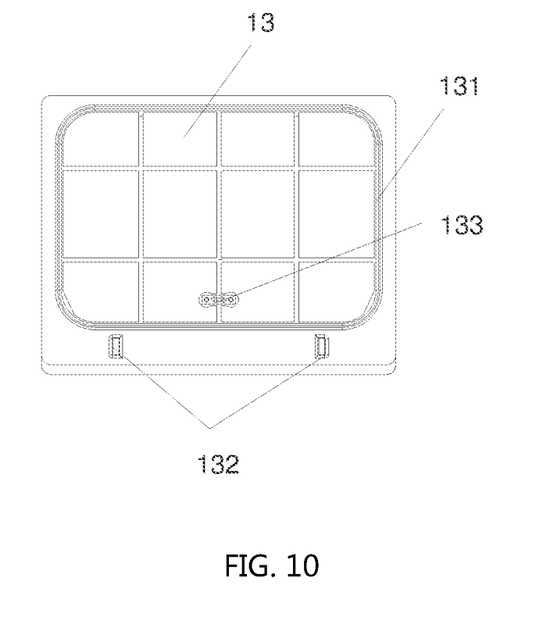
FIG. 10 is a schematic diagram showing a structure in a perspective according to the eighth embodiment of the present disclosure.

As shown in FIG. 9 and FIG. 10, on the basis of the first embodiment, the access hole for allowing the detection platform 2 in or out of the box body 1 is provided on the side wall of the detection box body 1. The access hole is sealed from the outside of the detection box body 1 with the box door 13. The linkage assembly 5 is arranged between the detection platform 2 and the box door 13. The linkage assembly 5 enables the box door 13 to be automatically opened or closed following the movement of the detection platform 2. A drive motor (not shown in the drawings) driving the detection platform 2 in or out of the detection box body 1 is arranged within the dark room of the detection box body 1. The light shielding portion is arranged between the detection box body 1 and the box door 13. The light shielding portion surrounds the outside of the access hole.

In this embodiment, the detection platform 2 is connected with the box door 13 by providing the linkage assembly 5. Moreover, when the detection platform 2 moves, the box door 13 is automatically opened or closed by the linkage assembly 5, so that the access hole is sealed. The linkage assembly is simple in structure without manual operation of a user. It is only necessary for driving the detection platform 2 by the driving motor to move and then tighten or loosen the box door 13, so that the box door 13 may be automatically opened or closed. According to the linkage assembly is convenient to use.

Further, in this embodiment, a light shielding portion is arranged between the detection box body 1 and the box door 13, and the light shielding portion surrounds the outside of the access hole for obstructing light to prevent light from entering the detection box body 1, so that the detection accuracy of the analyzer is influenced. Particularly, the light shielding portion may be arranged on the box door 13 or on the detection box body 1 or may be formed by combining two portions arranged on the box door 13 and on the detection box body 1, which is not limited here. When the box door 13 is closed, the driving motor may control the movement of the detection platform 2, and the detection platform 2 may tighten the box door 13 through the linkage assembly 5, so that the box door 13, the detection box body 1 and the light shielding portion are closely attached. Accordingly, a good light shielding effect is achieved.

Ninth Embodiment

Figure 11:
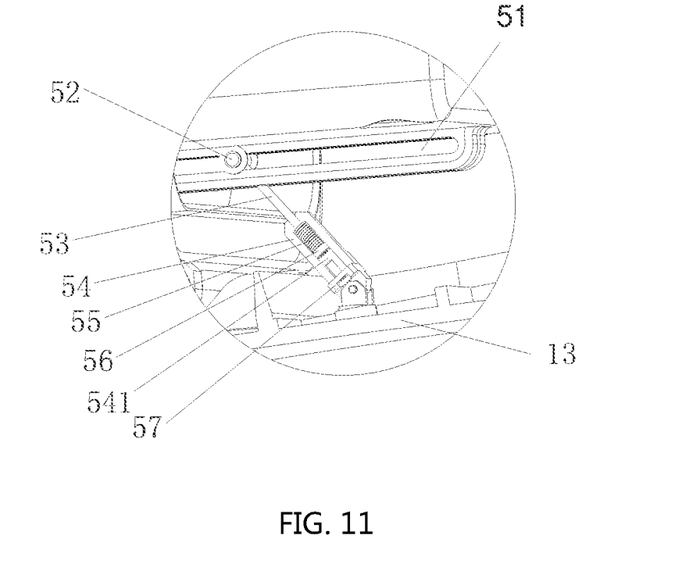
FIG. 11 is a schematic diagram showing a structure of a linkage assembly according to a ninth embodiment of the present disclosure.

As shown in FIG. 11, on the basis of the eighth embodiment, the linkage assembly 5 includes a sliding groove 51, which is provided on the detection platform 2 and configured to extend along a moving direction of the detection platform 2; a sliding shaft 52, which is configured to slide or rotate within the sliding groove 51; and a connecting rod 53, one end of which is fixedly connected with the sliding shaft 52 and the other end of which is pivotally connected with the box door 13, wherein a sleeve 54, a first spring 55 and a fixing ring 56 are sequentially sleeved on the connecting rod 53; the fixing ring 56 is fixed to the distal end of the connecting rod 53; an accommodating cavity 541 for accommodating the first spring 55 and the fixing ring 56 is arranged within the sleeve 54; and the sleeve 54 is pivotally connected with the box door 13.

Particularly, in this embodiment, a guide rail and a sliding block which are mutually matched are arranged between the detection platform 2 and the detection box body 1 to facilitate the driving motor to drive the detection platform 2 to move within the detection box body 1. As can be seen from FIG. 9, when the detection platform 2 moves within the detection box body 1, one end of the connecting rod 53 in the linkage assembly 5 slides within the sliding groove 51 through the sliding shaft 52, while in a sliding process, the other end of the connecting rod 53 may drive the box door 13 to rotate by a pivoting structure, so that the box door 13 is opened or closed.

In a specific implementation, since the driving motor has a stroke error when driving the detection platform 2 to move into the detection box body 1, the movement of the box door 13 has a corresponding error. If there is an insufficient actual stroke of the driving motor, the box door 13 is incapable of fully closing the access hole. If the actual stroke of the driving motor exceeds an actual stroke of the box door 13, it is possible for the box door 13 to be installed in place, and the driving motor is still performing a movement of a predetermined stroke, so that the motor in the driving motor is stuck. In this embodiment, in order to eliminate the risk caused by the error, the first spring 55 is sleeved on the connecting rod 53. In a process of driving the box door 13 to move by the connecting rod 43, the first spring 55 in the sleeve 54 may be compressed or elongated, and the stroke in which the detection platform 2 is driven by the driving motor to move may be slightly larger than the predetermined stroke of the box door 13, in this way, the actual movement stroke of the box door 13 will be larger than the predetermined stroke, so that when the linkage assembly 5 pulls the box door 13 to move, the first spring 55 may be elongated to meet the actual movement stroke, and thus it is possible to ensure that the box door 13 smoothly seals the detection box body 1 and prevents the motor in the driving motor from being stuck and the box door 13 from being uninstalled in place. Further, since the first spring 55 provided is elongated, when the driving motor drives the detection platform 2 to move towards the outside of the detection box body 1, an elastic force may control the box door 13 to be opened since the first spring 55 is previously elongated, effectively preventing the box door 13 from being stuck.

In this embodiment, a sealing cover 57 is arranged at an opening of the accommodating cavity 541, and pivotally connected with the box door 13. In this embodiment, the sealing cover 57 is configured to seal the opening of the accommodating cavity 541, limit a movement stroke of the first spring 55 and the fixing ring 56, and prevent the first spring 55 and the fixing ring 56 from being disengaged from the accommodating cavity 541.

A pivoting shaft is arranged on the connecting rod 53. The pivoting shaft is connected with the pivoting block 133 arranged on the box door 13, and thus it is possible for the connecting rod 533 to be pivotally connected with the box door 13 as well. It should be noted that the pivotal connection in this embodiment is not limited to a specific structural form, and may be implemented by using the most common manner of pivotal connection via a shaft hole.

Tenth Embodiment

Figure 12:
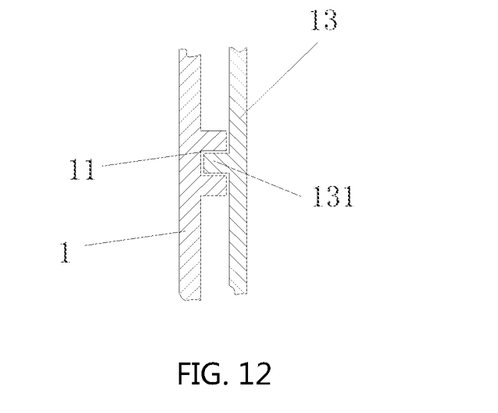
FIG. 12 is a schematic cross-sectional view showing a structure of a light shielding portion according to a tenth embodiment of the present disclosure.

As shown in FIG. 12, on the basis of the eighth embodiment, the light shielding portion includes a concave ring 11 and a convex ring 131 which are respectively arranged at the access hole of the detection box body 1 and on the box door 13 and mutually matched.

In this embodiment, the light shielding portion is composed of the concave ring 11 arranged at the periphery of the access hole of the detection box body 1 and the convex ring 131 arranged on the box door 13. When the box door 13 closes the access hole of the detection box body 1, the convex ring 131 on the box door 13 may be embedded in the concave ring 11 at the access hole of the detection box body 1, that is, the light shielding portion is formed, so that the access hole of the detection box body 1 is shielded from light. Accordingly, a good light shielding effect is achieved.

Preferably, in this embodiment, the concave ring 11 at the periphery of the access hole is formed by an outer wall of the detection box body 1. When the box door 13 seals the access hole of the detection box body 1, the convex ring 131 on the box door 13 is matched with the concave ring 11 at the access hole, and the convex ring 131 is embedded within the concave ring 11, so that light shielding is achieved. Certainly, the depth of the concave ring 11 may be set actually as required. The larger the depth of the concave ring 11 is set, the better the light shielding effect is, and the better it is possible for preventing light from entering the inside of the detection box body 1. Alternatively, in this embodiment, the size of the concave ring 11 is slightly larger than that of the convex ring 131, such that the convex ring 131 is squeezed into the concave ring 11, and a gap between the concave ring 11 and the convex ring 131 is small, so that the access hole is shielded from light well. Further, for the convenience of operation, two hinge portions 132 (as shown in FIG. 10) are further arranged at the lower portion of the box door 13, and matched with corresponding hole grooves at the access hole on the detection box body 1 for being hinged with the detection box body when the box body 13 is closed or opened. Further, it is further beneficial to fix the box door 13 on the detection box body 1, so as to prevent the box door 13 from falling off the detection box body 1.

In the embodiment of the present disclosure, the detection platform is arranged within the dark room, and the positioning module for fixing the microfluidic chip is arranged on the detection platform, so that the microfluidic chip is fixed within the dark room. The magnet module capable of automatically finely adjusting the height of the magnet is provided, and the height of the magnet is automatically adjusted according to the height of the magnetic bead channel of the microfluidic chip, so that the magnetic bead is precisely controlled. Moreover, the plurality of to-be-pressed portions of the microfluidic chip are pressed in a one-to-one correspondence manner by means of the plurality of motors, so that a pressing sequence may be arbitrarily adjusted as needed, so that the microfluidic chemiluminescence immunoassay analyzer is suitable for various microfluidic chips for different detection purposes. Compared with a large-scale fully automatic chemiluminescence instrument, the microfluidic chemiluminescence immunoassay analyzer provided by the embodiment of the present disclosure is greatly simplified in structure, small in volume, low in manufacturing cost, and convenient to operate. Compared with a semi-automatic chemiluminescence instrument, the microfluidic chemiluminescence immunoassay analyzer greatly reduces the artificial operation, so as to be relatively high in testing speed and relatively accurate in results. In the present disclosure, the detection platform is connected with the box door by providing the linkage assembly. When the detection platform moves, the box door is driven to be automatically opened or closed by the linkage assembly, so that the access hole is sealed. Accordingly, the linkage assembly is simple in structure without manual operation of a user. It is only necessary for driving the detection platform by the driving motor to move and further tighten or loosen the box door, so that the box door may be automatically opened or closed. Accordingly, the linkage assembly is convenient to use. When the box door is closed, the driving motor may control the detection platform to move, and the detection platform may tighten the box door by the linkage assembly, so that the box door, the detection box body and the light shielding portion are closely attached. Accordingly, a good light shielding effect is achieved.

The above descriptions are merely preferred embodiments of the present disclosure, and are not intended to limit the present disclosure. Any modifications, equivalent substitutions and improvements made within the spirit and principle of the present disclosure should be included within the scope of protection of the present disclosure.

What is claimed is:

1. A microfluidic chemiluminescence immunoassay analyzer, comprising:
    a detection box body provided with a dark room;
    a detection platform arranged within the dark room and configured to place a microfluidic chip, wherein a magnetic bead and a magnetic bead channel for placing the magnetic bead are arranged on the microfluidic chip;
    a magnet module arranged above the detection platform and being capable of adjusting the height of the magnet, wherein the magnet module is configured to collect and drag the magnetic bead within the magnetic bead channel;
    a pressing module arranged on the detection box body and configured to press a plurality of to-be-pressed portions of the microfluidic chip in a one-to-one correspondence manner by means of a plurality of motors; and
    a positioning module arranged on the detection platform and configured to fix the microfluidic chip;
    wherein the detection platform and the microfluidic chip are both fixed relative to the dark room.

2. The microfluidic chemiluminescence immunoassay analyzer according to claim 1, wherein the positioning module comprises:
    a first accommodating groove provided on the top of the detection platform and configured to place the microfluidic chip;
    an elastic positioning portion arranged on the inner wall of the first accommodating groove and configured to abut against a corner of the microfluidic chip, wherein the elastic positioning portion pushes the microfluidic chip to enable the microfluidic chip to abut against two adjacent side walls of the first accommodating portion, and the two adjacent side walls, which abut against the microfluidic chip, of the first accommodating groove form a positioning surface; and
    a vertical limiting portion arranged above the first accommodating groove and configured to fix the microfluidic chip.

3. The microfluidic chemiluminescence immunoassay analyzer according to claim 1, wherein the positioning module comprises:
    a second accommodating groove provided on the side wall of the detection platform and configured to place the microfluidic chip, wherein the microfluidic chip is inserted within the second accommodating groove from the outside of the detection box body;
    an elastic positioning pin arranged on the bottom surface of the second accommodating groove and configured to fix the microfluidic chip, wherein the elastic positioning pin is provided with a guiding surface on an insertion side of the microfluidic chip;
    an unlocking portion arranged on the side wall of the detection platform and configured to unlock the elastic positioning pin; and
    an ejection portion arranged within the dark room and configured to eject the microfluidic chip.

4. The microfluidic chemiluminescence immunoassay analyzer according to claim 1, wherein the magnet module comprises:
    a magnet, which is capable of sliding along the magnetic bead channel of the microfluidic chip after an end portion of the magnet abuts against the surface of the magnetic bead channel, so as to collect and drag the magnetic bead within the magnetic bead channel of the microfluidic chip;
    a mounting block configured to mount the magnet;
    a first driving mechanism configured to drive the mounting block and the magnet to move linearly;
    a second driving mechanism connected with the mounting block and configured to adjust the height of the mounting block; and
    a height adjusting mechanism arranged between the mounting block and the magnet and configured to automatically finely adjust the height of the magnet.

5. The microfluidic chemiluminescence immunoassay analyzer according to claim 4, wherein one end of the mounting block is connected with the second driving mechanism and an other end thereof is provided with a stepped hole for allowing the magnet to slide up and down, and the stepped hole forms the height adjusting mechanism; and
    wherein when the magnet slides along the magnetic bead channel, the height of the magnet is automatically finely adjusted while the magnet slides within the stepped hole.

6. The microfluidic chemiluminescence immunoassay analyzer according to claim 4, wherein the height adjusting mechanism comprises:
    a connecting block configured to fixedly connect the magnet; and
    a rotating shaft configured to connect the connecting block and the mounting block;
    wherein the connecting block rotates about a shaft core of the rotating shaft after being pivotally connected with the mounting block; and
    wherein when the magnet slides along the magnetic bead channel, the height of the magnet is automatically finely adjusted while the magnet rotates about the rotating shaft.

7. The microfluidic chemiluminescence immunoassay analyzer according to claim 1, wherein the pressing module comprises:

a mounting platform arranged above the detection platform;

a plurality of stepping motors, which are mounted on the mounting platform, wherein an adapter is connected to an output shaft of each stepping motor, a pressing block is connected to the other end of the adapter, and the pressing blocks are configured to press the plurality of to-be-pressed portions of the microfluidic chip in a one-to-one correspondence manner; and a controller, which is electrically connected with the plurality of stepping motors to control a pressing sequence of the output shafts of the stepping motors.

8. The microfluidic chemiluminescence immunoassay analyzer according to claim 1, wherein an access hole for allowing the detection platform in or out of the detection box body is provided on the side wall of the detection box body;

wherein the access hole is sealed from the outside of the detection box body with a box door;

wherein a linkage assembly is arranged between the detection platform and the box door, the linkage assembly enables the box door to be automatically opened or closed following the movement of the detection platform;

wherein a driving motor driving the detection platform in or out of the detection box body is arranged within the dark room of the detection box body; and wherein a light shielding portion is arranged between the detection box body and the box door, and the light shielding portion surrounds the outside of the access hole.

9. The microfluidic chemiluminescence immunoassay analyzer according to claim 8, wherein the linkage assembly comprises:

a sliding groove provided on the detection platform and configured to extend along a moving direction of the detection platform;

a sliding shaft configured to slide or rotate within the sliding groove; and a connecting rod, with one end fixedly connected with the sliding shaft and an other end pivotally connected with the box door; wherein a sleeve, a first spring and a fixing ring are sequentially sleeved on the connecting rod;

the fixing ring is fixed at a distal end of the other end of the connecting rod;

an accommodating cavity for accommodating the first spring and the fixing ring is defined within the sleeve; and the sleeve is pivotally connected with the box door.

10. The microfluidic chemiluminescence immunoassay analyzer according to claim 8, wherein the light shielding portion comprises a concave ring and a convex ring which are respectively arranged at the access hole of the detection box body and on the box door and are mutually matched.

11. The microfluidic chemiluminescence immunoassay analyzer according to claim 1, wherein various testing agents are loaded within the to-be-pressed portions.

12. The microfluidic chemiluminescence immunoassay analyzer according to claim 1, wherein the detection box body includes an upper box body, a lower box body and a box door, concave cavities are respectively arranged on the upper box body and the lower box body, the upper box body, the lower box body and the box door are fastened, a joint among the upper box body, and the lower box body and the box door is subjected to a light shielding treatment to form the dark room.

13. The microfluidic chemiluminescence immunoassay analyzer according to claim 10, wherein the light shielding treatment is placing a sealant at the joint among the upper box body, the lower box body and the box door.

14. The microfluidic chemiluminescence immunoassay analyzer according to claim 10, wherein the light shielding treatment is arranging a concave ring and a convex ring which are mutually matched on the joint among the upper box body, the lower box body and the box door.

15. The microfluidic chemiluminescence immunoassay analyzer according to claim 1, wherein further comprising a temperature control module, an optical signal detection module and a control circuit module.

16. The microfluidic chemiluminescence immunoassay analyzer according to claim 9, wherein the controller controls different stepping motors to drive the pressing blocks thereon to press the to-be-pressed portions of the microfluidic chip.

17. The microfluidic chemiluminescence immunoassay analyzer according to claim 9, wherein the pressing module further includes a sensor, which is electrically connected with the controller, wherein a triggering block corresponding to the sensor is arranged on the output shaft of the stepping motor.

18. The microfluidic chemiluminescence immunoassay analyzer according to claim 17, wherein the sensor is a photoelectric sensor.

* * * * *